US006613432B2

(12) United States Patent
Zamora et al.

(10) Patent No.: US 6,613,432 B2
(45) Date of Patent: Sep. 2, 2003

(54) PLASMA-DEPOSITED COATINGS, DEVICES AND METHODS

(75) Inventors: Paul O. Zamora, Gaithersburg, MD (US); Shigemasa Osaki, Sandy, UT (US); Meng Chen, Salt Lake City, UT (US)

(73) Assignee: BioSurface Engineering Technologies, Inc., College Park, MD (US)

( * ) Notice: Subject to any disclaimer, the term of this patent is extended or adjusted under 35 U.S.C. 154(b) by 113 days.

(21) Appl. No.: 09/746,234

(22) Filed: Dec. 21, 2000

(65) Prior Publication Data
US 2002/0009604 A1 Jan. 24, 2002

Related U.S. Application Data
(60) Provisional application No. 60/221,646, filed on Jul. 28, 2000, and provisional application No. 60/171,844, filed on Dec. 22, 1999.

(51) Int. Cl.⁷ .............................. B32B 15/04; B05D 3/00
(52) U.S. Cl. .................. 428/409; 427/2.24; 427/539; 428/457; 428/469; 428/544; 428/685
(58) Field of Search ................ 427/2.24, 539; 428/409, 457, 469, 544, 685

(56) References Cited

U.S. PATENT DOCUMENTS

| 5,062,900 A | * 11/1991 | Berneron et al. ............... 148/4 |
| 5,080,924 A | 1/1992 | Kamel et al. ................... 427/2 |
| 5,336,518 A | 8/1994 | Narayanan et al. ............ 623/1 |
| 5,338,770 A | 8/1994 | Winters et al. ............. 523/112 |
| 5,449,383 A | 9/1995 | Chatelier et al. ............... 623/1 |
| 5,463,010 A | 10/1995 | Hu et al. ....................... 528/25 |
| 5,662,960 A | 9/1997 | Hostettler et al. ............ 427/2.3 |
| 5,665,077 A | 9/1997 | Rosen et al. ................. 604/266 |
| 5,718,892 A | 2/1998 | Keefer et al. ............. 424/78.27 |
| 5,770,645 A | 6/1998 | Stamler et al. .............. 524/419 |
| 5,789,018 A | 8/1998 | Engelson et al. ............. 427/2.3 |
| 5,797,887 A | 8/1998 | Rosen et al. ................. 604/265 |
| 5,824,049 A | 10/1998 | Ragheb et al. .................. 623/1 |
| 5,876,452 A | 3/1999 | Athanasiou et al. ........... 623/16 |
| 5,919,570 A | 7/1999 | Hostettler et al. ........ 428/424.8 |
| 5,955,588 A | 9/1999 | Tsang et al. ................... 536/21 |
| 5,962,138 A | 10/1999 | Kolluri et al. ............ 428/411.1 |
| 5,994,444 A | 11/1999 | Trescony et al. ............ 524/429 |
| 6,017,577 A | 1/2000 | Hostettler et al. .......... 427/2.12 |
| 6,087,479 A | 7/2000 | Stamler et al. .............. 530/363 |
| 6,168,777 B1 | 1/2001 | Greff et al. ................. 424/1.25 |

OTHER PUBLICATIONS

Aronsson, B.O. et al. "Glow discharge plasma treatment for surface cleaning and modification of metallic biomaterials." J Biomed Mat Res, 1997, 35:49–73.

(List continued on next page.)

Primary Examiner—D. S. Nakarani
(74) Attorney, Agent, or Firm—Stephen A. Slusher; Peacock, Myers & Adams, PC

(57) ABSTRACT

Coatings, devices and methods are provided, wherein the contacting surface of a medical device with at least one contacting surface for contacting a bodily fluid or tissue is modified by plasma treatment in a plasma comprising nitrogen-containing molecules and oxygen-containing molecules. The nitrogen-containing molecules include $NH_3$, $(NH_4)^+$, $N_2O$, $NO$, $NO_2$ and $N_2O_4$, and the oxygen-containing molecules include $O_2$ and $O_3$. The plasma-modified contacting surface exhibits decreased adhesion of at least some mammalian cells, such as platelets and leukocytes, decreased restenosis when used with stents, and increased apoptosis. Additional layers may be applied, including plasma polymerized hydrocyclosiloxane monomers, amine-providing groups such as N-trimethylsilyl-allylamine, polyoxyalkylene tethers, and bioactive compounds.

37 Claims, 7 Drawing Sheets

OTHER PUBLICATIONS

Baumbach, A. et al. "Local Drug Delivery: Impact of Pressure, Substance Characteristics, and Stenting on Drug Transfer Into the Arterial Wall." Catheter Cardiocase Interv 1999, 47:102–6.

Kruse, K.R. et al. "Local Drug Delivery of Argatroban From a Polymeric–Metallic Composite Stent Reduces Platelet Deposition in a Swine Coronary Model." Catheter Cardiovasc Interv 1999, 46:503–7.

Mowery, K.A. et al. "Preparation and characterization of hydrophobic polymeric films that are thromboresistant via nitric oxide release." Biomaterials 2000,21:9–21.

Santos, R.M. et al. "Local Administration of L–703,081 Using a Composite Polymeric Stent Reduces Platelet Deposition in Cannine Coronary Ateries." Am J Cardiol 1998, 82:673–5, A8.

Sly, M.K, et al. "Inhibition of Surface–Induces Platelet Activation by Nitric Oxide." ASAIO Journal 1995, 41:M394–9.

Yamawaki, T. et al. "Intramural Delivery of a Specific Tyrosine Kinase Inhibitor With Biodegradable Stent Suppresses the Restenotic Changes of the Coronary Artery in Pigs in Vivo." J Am Coll Cardiol 1998, 32:780–6.

* cited by examiner

PLASMA-DEPOSITED COATINGS, DEVICES AND METHODS

CROSS-REFERENCE TO RELATED APPLICATIONS

This application claims the benefit of the filing of U.S. Provisional Patent Application Ser. No. 60/171,844, entitled METHOD AND COATING TO INHIBIT RESTENOSIS, to Paul O. Zamora, Shugemasa Osaki and Meng Chen, filed on Dec. 22, 1999, and of U.S. Provisional Patent Application Ser. No. 60/221,646, entitled PLASMA DEPOSITION OF BIOACTIVE NITROGEN-CONTAINING AGENTS APPLICATIONS AND METHODS, to Paul O. Zamora, Shigemasa Osaki and Meng Chen, filed on Jul. 28, 2000, and the specifications of both are incorporated herein by reference.

BACKGROUND OF THE INVENTION

1. Field of the Invention (Technical Field)

This invention relates to applications and methods for plasma treatment of coatings for enhanced biocompatible properties for implanted medical devices, including decreased restenosis and decreased adhesion of cells, such as platelets and leukocytes. The invention further relates to coated medical devices and methods, which include plasma-deposited nitrogen-containing and oxygen-containing coatings, and one or more additional coatings, including siloxane-containing coatings, polyethylene glycol-containing coatings and dextran-containing coatings.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

There is a need for coatings and surfaces of medical devices that limit or inhibit restenosis and attachment of cells, particularly attachment of platelets, leukocytes and similar cells. Medical devices, particularly implantable medical devices, frequently result in platelet attachment leading to thrombosis, leukocyte attachment leading to inflammation, and aberrant cellular in-growth leading to fibrosis and related conditions. For example, restenosis is a common problem following stent placement, involving overpopulation by smooth muscle cells with consequent re-narrowing of the lumen of the blood vessel. With stents and other blood-contacting medical devices, including catheters and similar devices, attachment of platelets and leukocytes is a significant problem. Substantial effort has been devoted to finding materials, coatings, surfactants, drugs and other substances that will inhibit either restenosis or attachment of cells.

Implantable medical devices are used for a wide variety of purposes. Thus devices such as stents, shunts, catheters, prosthetic heart valves, pacemakers, pulse generators, cardiac defibrillators, and similar devices and components are used in the treatment of cardiac and other diseases. A variety of screws, anchors, plates, joints and similar devices are used in orthopedic surgery. Catheters, drains, shunts, leads, stimulators, sensors, seeds, inducers and other devices are used in a wide variety of applications. These implantable medical devices are made from a wide variety of materials, including metals, plastics and various polymeric materials.

A large number of coatings have been explored for used with implantable medical devices to improve the biocompatibility or otherwise improve the in vivo behavior of the implant. U.S. Pat. No. 5,338,770 describes methods and materials for coating biomedical devices and implants with poly (ethylene oxide) chains suitable for covalent attachment of bioactive molecules intended to counteract blood-material incompatibility. U.S. Pat. No. 5,463,010 describes membranes, including polymerized aliphatic hydrocyclosiloxane monomers, for use in coating biomedical devices and implants, and suitable for use as a substrate for covalent attachment of other molecules. U.S. Pat. No. 5,824,049 describes multiple-layer coatings, providing for controlled release of a drug or other bioactive materials through a porous layer. U.S. Pat. No. 6,017,577 describes a polyurethane hydrogel coating for use in medical devices. These and a number of other references known in the art provide for some form of coating, and optionally a specific bioactive layer or coating, for use in improving biocompatibility. However, none of these methods or compositions has addressed all of the problems encountered with implantable medical devices, such as restenosis with stents and attachment of platelets and leukocytes, and none have resulted in widespread commercial and industrial acceptance.

There has been interest in use of a variety of substances in medical device coatings to decrease restenosis, cellular attachment or provide other biomedical benefits. For example, U.S. Pat. No. 6,087,479 discloses coatings, such as a nylon or plastic matrix coating, for use with nitric oxide adducts, such as sodium nitroprusside, and U.S. Pat. No. 5,665,077 discloses polymeric coatings with nitroso compounds. A number of articles in the scientific literature disclose related methods, for example, see Mowery K A et al: Preparation and characterization of hydrophobic polymeric films that are thromboresistant via nitric oxide release. *Biomaterials* 2000; 21:9–21; and Sly M K et al: Inhibition of surface-induced platelet activation by nitric oxide. *ASAIO J* 1995 41:M394–8.

A recognized problem with stents, and particularly coated stents, is that the coating itself induces an inflammatory response or a thrombogenic response, either of which can lead to unwanted biological consequences. Furthermore, both inflammatory responses and thrombogenic responses appear to be implicated in restenosis in that these responses elicit local production or secretion of growth factors, leading to restenosis. A large number of agents have been investigated, used both systemically and locally, to overcome these responses. Tranilast is one such agent, and is a small molecule with a number of biological actions. It is used in Japan as an anti-allergy drug and acts as an anti-inflammatory on mast cells. It also inhibits arterial smooth muscle cell proliferation and migration in vitro and restenosis in vivo. It is currently under evaluation in clinical trials as a systemic agent to limit restenosis following balloon angioplasty. Pactitaxel (taxol) has also been described as having a beneficial effect following local administration, including when used in a stent coating (Herdeg et al. *Semin Interv Cardiol* 1999, 3:197–9; Baumbach et al., *Catheter Cardiovasc Interv* 1999, 47:1026). Also, local administration of a glycoprotein IIb/IIIa receptor antagonist or anti-thrombin agent stents reportedly reduced platelet deposition in coronary arteries (Santos et al. *Am J Cardiol* 1998, 82:673–5, A8; Kruse *Catheter Cardiovasc Interv* 1999, 46:503–7). Intramural delivery of a specific tyrosine kinase inhibitor with a biodegradable stent reportedly suppressed restenotic changes of the coronary artery in pigs in vivo (Yamawaki et al *J Am Coll Cardiol* 1998, 32:780–6). Also, dexamethazone has been delivered locally with stents (Lincoff et al. *J Am Coll Cardiol* 1997, 29:808–16; Strecker *Cardiovasc Intervent Radiol* 1998, 21(6): 487–96).

Plasma processes have been used in manufacture of medical devices, primarily for use in surface cleaning and preparation methods (Aronsson et al., *J Biomed Mat Res* 1997, 35:49–73). However, plasma processes have also been used to introduce groups, such as amine groups, into a surface, as described in U.S. Pat. No. 5,338,770. That patent describes a method of introduction of amine groups using ammonia gas in the plasma chamber at a flow rate of 190 micromoles per second at 170 mTorr absolute pressure, with the target, hollow fibers, exposed to 180 watts at a radio frequency of 13.56 MHz for fifteen minutes. Plasma processes have also been used to introduce various coatings and polymeric groups, as described generally in U.S. Pat. Nos. 5,463,010 (hydrocyclosiloxane membrane), 5,336,518 (heptafluorobutylmethacrylate membrane), 5,962,138 (plasma film layers of various monomers), and other references. However, none of these processes have demonstrated both decreased restenosis and decreased attachment of cells such as platelets and leukocytes when used in vivo.

Thus it would be desirable to provide coatings for surfaces of medical devices which exhibit decreased restenosis and decreased attachment of cells. In particular, it would be desirable to provide methods for preparing and fabricating devices and substrates for treating or preventing hyperplasia, inflammation, thrombosis, and other disease conditions. The methods should be useful with both permanently implanted devices, such as vascular stents, grafts, and coils, as well as temporarily implanted devices, such as catheters, wires, pellets, and the like. The fabrication methods should be convenient, economical, and efficacious.

However, notwithstanding the work that has been done, a simple and reliable method of causing stents, catheters and other medical devices to inhibit cellular attachment, and in the case of stents and other devices within a blood vessel, to inhibit restenosis, has still not been demonstrated. This invention addresses that specific need.

SUMMARY OF THE INVENTION
(DISCLOSURE OF THE INVENTION)

The invention provides an implantable medical device with a plasma-modified surface, which medical device has at least one contacting surface for contacting a bodily fluid or tissue, wherein the contacting surface is modified by plasma treatment in a plasma including nitrogen-containing molecules and oxygen-containing molecules. In one embodiment, the nitrogen-containing molecules each comprise no more than six atoms, and preferably four or fewer atoms. The nitrogen-containing molecules may include $NH_3$, $NH_4$, $N_2O$, $NO$, $NO_2$ and $N_2O_4$. The oxygen-containing molecules may include $O_2$ and $O_3$. The plasma treatment with the nitrogen-containing molecules and the oxygen-containing molecules may be simultaneous. In the device, the plasma-modified contacting surface exhibits decreased adhesion of at least some mammalian cells, compared to a similar contacting surface that is not plasma-modified. The mammalian cells may be platelets or leukocytes.

The medical device may be a stent wherein the at least one contacting surface includes at least the lumen of the stent. The plasma-modified contacting surface comprising the lumen of the stent exhibits decreased restenosis subsequent to placement in a blood vessel, compared to a similar stent that is not plasma-modified.

The plasma treatment is for less than about five minutes, preferably for less than about two minutes, more preferably for less than about one minute, and most preferably for between about thirty seconds and about one minute.

In one embodiment, the plasma treatment is of a plasma wherein the nitrogen-containing molecules are $NH_3$ and the oxygen-containing molecules are $O_2$. The mass flow rate during plasma treatment with each of $NH_3$ and of $O_2$ is between a ratio of about 1.5:1 and about 1:1.5. In an alternative embodiment, the plasma treatment is of a plasma wherein the nitrogen-containing molecules are $N_2O$ and the oxygen-containing molecules are $O_2$. The mass flow rate during plasma treatment with each of $N_2O$ and of $O_2$ is between a ratio of about 1.5:1 and about 1:1.5.

The medical devices of this invention include stents, catheters, balloons, shunts, valves, pacemakers, pulse generators, cardiac defibrillators, spinal stimulators, brain stimulators, sacral nerve stimulators, leads, inducers, sensors, seeds, screws, anchors, plates and joints. The at least one contacting surface may be a metallic material, or may be a polymeric material. If it is a polymeric material, it may be biodegradable.

The device can further include a biologically compatible coating deposited over the plasma including nitrogen-containing molecules and oxygen-containing molecules. In one embodiment, the biologically compatible coating is a membrane formed from the plasma polymerization of hydrocyclosiloxane monomer of the general formula:

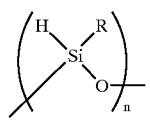

wherein R is an aliphatic group having 1 to about 5 carbon atoms and n is an integer from 2 to about 10. This hydrocyclosiloxane monomer may be 1,3,5,7-tetramethylhydrocyclotetrasiloxane, 1,3,5,7,9-pentamethylhydrocyclopentasiloxane, 1,3,5,7,9,11-hexamethylhydrocyclohexasiloxane, or a mixture of 1,3,5,7,9-pentamethylcyclopentasiloxane and 1,3,5,7,9,11-hexamethylcyclohexasiloxane monomers.

In an alternative embodiment, the biologically compatible coating may be a polymer or co-polymer, such as poly acrylate, poly bisphenol A carbonate, polybutadiene, polycarbonate, poly butylene terephthalate, poly butryl methacrylate, polydimethyl siloxane, polyester, polyethyleneimine, poly methyl methacrylate, polypropylene, polystyrene, polysulfone, polyurethane, poly vinyl, poly vinyl acetate polylactide, polyglycolide, polycaprolactone, or polyvinylidine fluoride.

The invention further consists of a coating for an implantable medical device with at least one contacting surface for contacting a bodily fluid or tissue, which coating includes a first layer on the contacting surface that include the product of plasma treatment with a plasma comprising nitrogen-containing molecules and oxygen-containing molecules. The coating may further include a second layer posited over the first layer, which second layer includes the product of plasma polymerization of hydrocyclosiloxane monomer of the general formula:

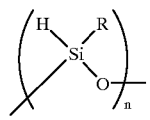

wherein R is an aliphatic group having 1 to about 5 carbon atoms and n is an integer from 2 to about 10. The coating may further include a third layer posited over the second layer, which third layer includes the product of plasma polymerization of monomers such as fluorocarbon monomers, organo-based monomers such as ethylene, allylamine, N-trimethylsilyl-allylamine, hydrocarbons, N-protected unsaturated amines, N-unprotected unsaturated amines, N-protected cyclic aliphatic amines, N-unprotected cyclic aliphatic amines, mercaptans, nitriles and organophosphorus compounds; and functionalizing monomers such as $N_2$, $CO_2$, $NH_3$ and $SO_2$. This coating may also include a polyoxyalkylene tether of the formula:

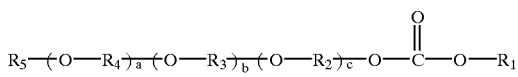

wherein $R_1$ is selected from an N-benzotriazole group, an N-2-pyrrolidinone group, or an 2-oxypyrimidine group; $R_2$, $R_3$ and $R_4$ are independently selected alkylene groups of about 2 to about 3 carbon atoms and may be the same or different; $R_5$ is selected from hydrogen, methyl, a carbonyloxy-N-benzotriazole group, a carbonyloxy-N-2-pyrrolidinone group, and a carbonyl-2-oxypyrimidine group; a is an integer from 1 to 1000 and each of b and c is an integer from 0 to 1000, where a+b+c is an integer from 3 to 1000, under conditions whereby the $R_5$ group reacts with a free amino group of the third layer thereby forming a covalent bond to give a modified polymeric surface having activated polyoxyalkylene groups covalently bonded thereto. One or bioactive compounds, including an aminoglycan polysaccharide, an amino polysaccharide, a peptide, a polypeptide, a protein, a compound having anti-thrombotic or thrombolytic properties, a compound having anti-inflammatory properties, a compound having cytostatic properties, a compound having cytotoxic properties, or a metal chelator, may be covalently bonded to the activated polyoxyalkylene groups of the polyoxyalkylene tether.

In one embodiment of the coating, the nitrogen-containing molecules each comprise no more than six atoms, and preferably four or fewer atoms. The nitrogen-containing molecules may include $NH_3$, $(NH_4)^+$, $N_2O$, $NO$, $NO_2$ and $N_2O_4$. The oxygen-containing molecules may include $O_2$ and $O_3$. The plasma treatment with the nitrogen-containing molecules and the oxygen-containing molecules may be simultaneous. The plasma treatment for the coating is for less than about five minutes, preferably for less than about two minutes, more preferably for less than about one minute, and most preferably for between about thirty seconds and about one minute.

In one embodiment, the plasma treatment is of a plasma wherein the nitrogen-containing molecules are $NH_3$ and the oxygen-containing molecules are $O_2$. The mass flow rate during plasma treatment of each of $NH_3$ and of $O_2$ is between a ratio of about 1.5:1 and about 1:1.5. In an alternative embodiment, the plasma treatment is with a plasma wherein the nitrogen-containing molecules are $N_2O$ and the oxygen-containing molecules are $O_2$. The mass flow rate during plasma treatment of each of $N_2O$ and of $O_2$ is between a ratio of about 1.5:1 and about 1:1.5.

The hydrocyclosiloxane monomer of the second layer of the coating may be 1,3,5,7-tetramethylhydrocyclotetrasiloxane, 1,3,5,7,9-pentamethylhydrocyclopentasiloxane, 1,3,5,7, 9,11-hexamethylhydrocyclohexasiloxane, or a mixture of 1,3,5,7,9-pentamethylcyclopentasiloxane and 1,3,5,7,9,11-hexamethylcyclohexasiloxane monomers.

In an alternative embodiment, the second layer of the coating may be a polymer or co-polymer such as poly acrylate, poly bisphenol A carbonate, polybutadiene, polycarbonate, poly butylene terephthalate, poly butryl methacrylate, polydimethyl siloxane, polyester, polyethyleneimine, poly methyl methacrylate, polypropylene, polystyrene, polysulfone, polyurethane, poly vinyl, poly vinyl acetate, polylactide, polyglycolide, polycaprolactone or polyvinylidine fluoride.

In the embodiment in which a polyoxyalkylene tether is applied to the third layer, it may be a polyethylene glycol. In one embodiment, the polyoxyalkylene tether is poly (oxythylene)-(N-hydroxybenzotriazolyl). The bioactive compound may be amino dextran or another complex polysaccharide or amino glycan.

The invention further includes implantable medical devices with at least one contacting surface for contacting a bodily fluid or tissue, wherein the contacting surface comprises a coating of any one of the first layer, the first layer and any one of the second layers, or the first layer, any one of the second layers, and any one of the third layers. Such devices may be stents, catheters, balloons, shunts, valves, pacemakers, pulse generators, cardiac defibrillators, spinal stimulators, brain stimulators, sacral nerve stimulators, leads, inducers, sensors, seeds, anti-adhesion sheets, screws, anchors, plates or joints, among other exemplary medical devices. The at least one contacting surface may be a metallic material or a polymeric material.

The invention further provides a method of imparting bioactive properties to a surface by modifying the surface by plasma treatment with a plasma comprising nitrogen-containing molecules and oxygen-containing molecules. In one embodiment of the method, the nitrogen-containing molecules each comprise no more than six atoms, and preferably four or fewer atoms. The nitrogen-containing molecules may include $NH_3$, $(NH_4)^+$, $N_2O$, $NO$, $NO_2$ and $N_2O_4$. The oxygen-containing molecules may include $O_2$ and $O_3$. The plasma treatment with the nitrogen-containing molecules and the oxygen-containing molecules may be simultaneous. In the method, the plasma-modified contacting surface exhibits decreased adhesion of at least some mammalian cells, compared to a similar contacting surface that is not plasma-modified. The mammalian cells may be platelets or leukocytes. The plasma treatment is for less than about five minutes, preferably for less than about two minutes, more preferably for less than about one minute, and most preferably for between about thirty seconds and about one minute.

In one embodiment of the method, the plasma treatment is with a plasma wherein the nitrogen-containing molecules are $NH_3$ and the oxygen-containing molecules are $O_2$. The mass flow rate during plasma treatment with each of $NH_3$ and of $O_2$ is between a ratio of about 1.5:1 and about 1:1.5. In an alternative embodiment, the plasma treatment is with a plasma wherein the nitrogen-containing molecules are $N_2O$ and the oxygen-containing molecules are $O_2$. The mass flow rate during plasma treatment with each of $N_2O$ and of $O_2$ is between a ratio of about 1.5:1 and about 1:1.5.

The method can also include the step of applying a biologically compatible coating subsequent to modifying the surface by plasma treatment. The biologically compatible coating is made by plasma polymerization of hydrocyclosiloxane monomer of the general formula:

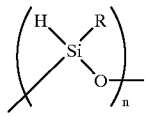

where R is an aliphatic group having 1 to about 5 carbon atoms and n is an integer from 2 to about 10. The hydrocyclosiloxane monomer may be 1,3,5,7-tetramethylhydrocyclotetrasiloxane, 1,3,5,7,9-pentamethylhyd rocyclopentasiloxane, 1,3,5,7,9,11-hexamethylhydrocyclohexasiloxane, or a mixture of 1,3,5,7,9-pentamethylcyclopentasiloxane and 1,3,5,7,9,11-hexamethylcyclohexasiloxane monomers.

In an alternative embodiment of the method, the biologically compatible coating may be a polymer or co-polymer such as poly acrylate, poly bisphenol A carbonate, polybutadiene, polycarbonate, poly butylene terephthalate, poly butryl methacrylate, polydimethyl siloxane, polyester, polyethyleneimine, poly methyl methacrylate, polypropylene, polystyrene, polysulfone, polyurethane, poly vinyl, poly vinyl acetate, polyglycolide, polylactide, polycaprolactone, or polyvinyledine fluoride.

If the biologically compatible coating is made by plasma polymerization of hydrocyclosiloxane monomer, the method may further include plasma polymerization of monomers such as fluorocarbon monomers, organo-based monomers such as ethylene, allylamine, N-trimethylsilyl-allylamine, hydrocarbons, N-protected unsaturated amines, N-unprotected unsaturated amines, N-protected cyclic aliphatic amines, N-unprotected cyclic aliphatic amines, mercaptans, nitriles and organophosphorus compounds; and functionalizing monomers such as $N_2$, $CO_2$, $NH_3$ and $SO_2$.

The coating may also include covalently bonding a polyoxyalkylene tether of the formula:

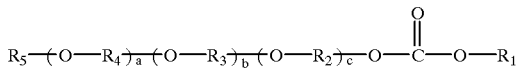

wherein $R_1$ is selected from an N-benzotriazole group, an N-2-pyrrolidinone group, or an 2-oxypyrimidine group; $R_2$, $R_3$ and $R_4$ are independently selected alkylene groups of about 2 to about 3 carbon atoms and may be the same or different; $R_5$ is selected from hydrogen, methyl, a carbonyloxy-N-benzotriazole group, a carbonyloxy-N-2-pyrrolidinone group, and a carbonyl-2-oxypyrimidine group; a is an integer from 1 to 1000 and each of b and c is an integer from 0 to 1000, where a+b+c is an integer from 3 to 1000, under conditions whereby the $R_5$ group reacts with a free amino group of a monomer, thereby forming a covalent bond to give a modified polymeric surface having activated polyoxyalkylene groups covalently bonded thereto. A bioactive compound may then be covalently bonded to the activated polyoxyalkylene groups of the polyoxyalkylene tether, using such bioactive compounds as aminoglycan polysaccharide, amino polysaccharide, peptides, polypeptides, proteins, compounds having anti-thrombotic or thrombolytic properties, compounds having anti-inflammatory properties, compounds having cytostatic properties, a compound having cytotoxic properties, and metal chelators.

A primary object of the present invention is to provide a plasma-deposited surface including a nitrogen-containing molecular species and an oxygen-containing molecular species wherein the resulting surface exhibits decreased cellular adhesion or increased cellular apoptosis.

Another object of the present invention is to provide modified surface of a medical device that includes one or more species of nitrogen-containing elements wherein the surface exhibits decreased cellular adhesion or increased cellular apoptosis.

Another object of the present invention is to provide a plasma-deposited surface including a nitrogen-containing molecular species and an oxygen-containing molecular species wherein the resulting surface, when applied to a stent or other vascular device, exhibits decreased restenosis concomitant with decreased cellular adhesion or increased cellular apoptosis.

Another object of the present invention is to provide modified surface of a vascular medical device, such as a stent, that includes one or more species of nitrogen-containing elements wherein the surface exhibits decreased restenosis and decreased cellular adhesion or increased cellular apoptosis.

Another object of the present invention is to provide a method for modifying, by plasma glow discharge, a surface of a medical device by means of simultaneous plasma treatment with $NH_3$ and $O_2$.

Another object of the present invention is to provide a method for modifying, by plasma glow discharge, a surface of a medical device by means of simultaneous plasma treatment with $N_2O$ and $O_2$.

Another object of the present invention is to provide a method for modifying, by plasma glow discharge, a surface of a medical device by means of simultaneous plasma treatment with a nitrogen-containing molecular species and an oxygen-containing molecular species for a period of less than five minutes, preferably less than one minute, and most preferably between about thirty seconds and one minute.

Another object of the present invention is to provide a method for modifying, by plasma glow discharge, a surface of a medical device by means of simultaneous plasma treatment with approximately equal quantities, by mass flow rates, of a nitrogen-containing molecular species and an oxygen-containing molecular species.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS

BEST MODES FOR CARRYING OUT THE INVENTION

Figure 1:
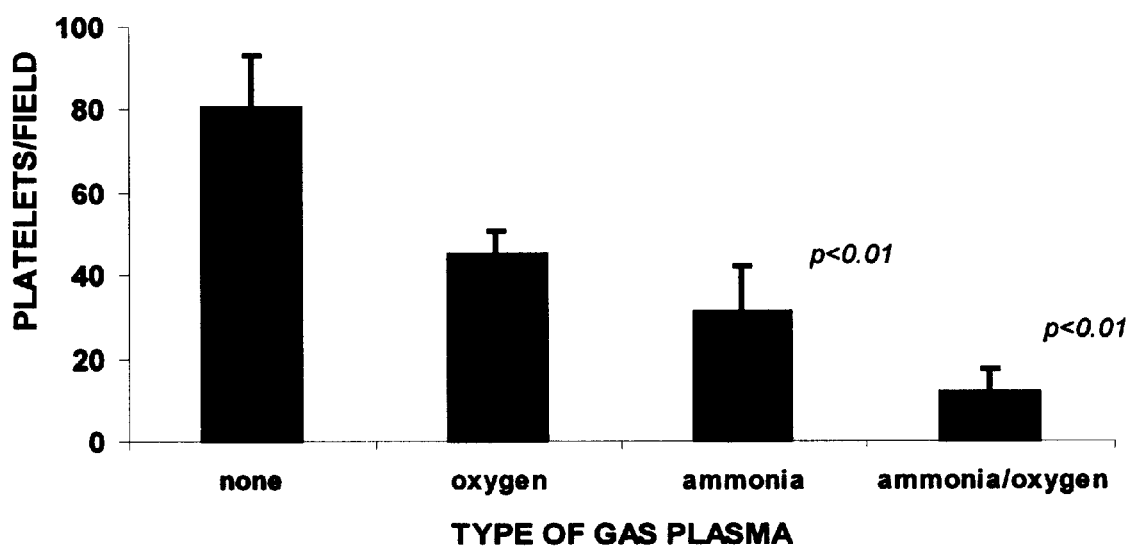
FIG. 1 is a bar graph depicting the attachment of human platelets to stainless steel with and without various gas plasma treatments. Platelets, as platelet-rich plasma in tissue culture medium, were incubated with stainless steel coupons for 1 hour at 37° C. after which the specimens were processed for fluorescence microscopy. Data is presented as the average number of platelets/micrograph field ±S.E. and is similar to results from two additional experiments. Paired t-test was used to assess statistical significance relative to untreated stainless steel.

The invention comprises a structural component with a surface, a gas plasma composed of molecular species containing oxygen and nitrogen, a method of exposing the structural component to the plasma, and a structural component with a surface modified by the plasma with resultant desirable or medically-useful properties.

Suitable structural components with a surface include medical devices that are intended to contact blood or other tissues, such as stents, catheters, shunts, grafts, and other medical devices known in the art. The structural component may include a mesh, coil, wire, inflatable balloon, or any other device or structure which is capable of being implanted at a target location, including intravascular target locations, intralumenal target locations, target locations within solid tissue, such as for the treatment of tumors, and the like. The implantable device can be intended for permanent or temporary implantation. Such devices may be delivered by or incorporated into intravascular and other medical catheters.

Suitable surfaces include stainless steel, nitinol, titanium, other metal alloys, polyvinyl chloride, polyethylene, polylactide, poly glycolide, poly caprolactone, poly methyl methacrylate, poly hydroxylethyl methacrylate, polyurethane, polystyrene, polycarbonate, dacron, extended poly tetrafluoroethylene (Teflon®), related fluoropolymer composites (Gore-Tex®), or combinations thereof. All or part of the available surface can be modified. Other substrate materials can also be used, including poly acrylate, poly bisphenol A carbonate, polybutadiene, poly butylene terephthalate, poly butryl methacrylate, polydimethyl siloxane, polyester, polyethyleneimine, polysulfone, poly vinyl acetate, polyvinylidine fluoride, polylactide, poly glycolide, poly caprolactone and copolymers and variants thereof.

A suitable method of exposing the structural components with a surface to the plasma involves placement of the structural components in a plasma field singly, in groups, or by methods involving fluidized bed or the like. Any number of flow-through techniques involving a vacuum may introduce the materials producing the plasma. Length of time in the plasma, gas composition, gas sequence, strength of any applied electrical field, or strength of any applied vacuum, either independently or in combination, can be varied as is required to attain the desired surface modification.

The result of the surface modification may include modulation of the attachment character of blood cells or blood components, alteration in the attachment character of blood or tissue proteins, and induction of cellular apoptosis or cytotoxicity. The surface modification may also augment concurrent pharmacological interventions, such as by co-administration with systemic drugs, co-administration with locally delivered drugs, the addition of one or more drugs or pro-drugs to the coating and similar interventions.

Suitable materials for producing the plasma include mixtures of oxygen plus any one of ammonia, nitrous oxide (dinitrogen oxide), nitrogen dioxide, nitrogen tetroxide, ammonium hydroxide, nitrous acid, mixtures thereof, or sequential use of two or more of the materials within a plasma. Ozone may also be used in place of oxygen. It is also contemplated that mixtures of oxygen and nitrogen can be used. When a gas mixture is used, the ratio of the component gases may be varied to obtain an optimal concentration of each gas. Also, the gases may be used serially. For example, ammonia plasma may be generated first, followed by a plasma of oxygen.

In a preferred embodiment, the method of treating surfaces with the plasma utilizes a reactant gas mixture of ammonia and oxygen (hereafter an $NH_3/O_2$ plasma) at a plasma treatment temperature of less than 100° C., and preferably at ambient temperature. The reactant gas mixture is introduced into the plasma chamber through a gas inlet manifold. The gas inlet manifold may also be an electrode. The gas inlet manifold is one plate of a parallel plate plasma chamber for introducing the gas mixture into the chamber.

The plate has a plurality of apertures, each comprising an outlet at a chamber or processing side of the plate and an inlet spaced from the processing side, with the entire plate complex being removable for ease of cleaning. The gas inlet manifold enhances the mixing of the gases.

The following terms are defined as follows for the purposes of this disclosure:

Bioactive Properties: performs in harmony with living tissue and/or blood, imparting one or more desired results or properties.

Plasma Polymerization: The formation of polymeric materials under the influence of plasma (consisting of ionized gases, free radicals and electrons).

Plasma Copolymerization: plasma polymerization of a mixture of different monomers.

Plasma Glow Zone: The region in which the glow discharge in the plasma polymerization process takes place.

Plasma Process

A capacitively coupled plasma deposition system may be used. In one embodiment, a glow discharge is ignited between seven-inch square parallel plate electrodes made of aluminum. The distance between the two electrodes is 6.5 inches. The electrodes are both power driven at a radio frequency of 13.56 MHz, and the whole plasma chamber is grounded. The sample rack is made of Teflon and stainless steel set in the plasma glow zone and is electrically floating, and may be rotated during the plasma process to assure uniformity of plasma coating or surface modification on samples.

In one embodiment, the device is placed within the plasma chamber, and the plasma chamber is evacuated to a base pressure of about 10 mTorr. A plasma is generated at 110 W and 50 mTorr for about 45 seconds using a mixture of $NH_3$ and $O_2$ at a total mass flow rate of 50 standard cubic centimeters per minute (sccm), resulting from a mass flow rate of 10 sccm of $NH_3$ and 15 sccm of $O_2$. Decreased attachment of lymphocytes and platelets is observed on substrates subjected to this treatment.

In another embodiment, the plasma is generated for approximately forty-five seconds at 110 W at 50 mTorr using a mass flow rate of 40 sccm for $NH_3$ and 10 sccm for $O_2$.

In yet another embodiment, plasma was generated at 110 W under a vacuum of 50 mTorr and using a mass flow rate of 25 sccm of $N_2O$ and 25 sccm of $O_2$. Decreased attachment of lymphocytes and platelets, together with increased apoptosis, is observed on stainless steel subjected to this plasma treatment.

Substantially decreased restenosis and cellular attachment, together with increased apoptosis, is observed utilizing the foregoing general reaction conditions. By contrast, pronounced restenosis and cellular attachment is observed when the initial $NH_3/O_2$ plasma treatment is either significantly longer or shorter. The preferred plasma treatment is for less than about five minutes, preferably for less than about two minutes, and most preferably for between about thirty seconds and about one minute. Utilizing steel wafers and plasma treatment with $NH_3/O_2$ for varying times from zero seconds through 420 seconds, an increase in the amount of apoptosis was observed up to about 45 seconds, after which the apoptotic activity decreased.

Elemental surface composition was determined by x-ray photoelectron spectroscopy of stainless steel wafers both without a plasma treatment and with a plasma treatment. The plasma treatment consisted of either a 45 second exposure to a mixed gas composed of 20 sccm $NH_3$ and 30 sccm $O_2$ or 25 sccm $N_2O$ and 25 sccm $O_2$. The values are reported in TABLE 1 in atomic percent and are for elements above atomic number 2 within 50 Å of the surface. The nitrogen content is highest in the specimen treated with $NH_3/O_2$ plasma and lowest on the untreated specimen.

TABLE 1

| Plasma type | ELEMENTAL SURFACE COMPOSITION IN ATOMIC % | | | | | | | | | | |
| --- | --- | --- | --- | --- | --- | --- | --- | --- | --- | --- | --- |
| | C | N | O | F | Si | S | Cl | Cr | Fe | Ni | Mo |
| None | 21.9 | 0.5 | 52.5 | 0.6 | 1.9 | 1.0 | 0.2 | 10.7 | 9.5 | 1.1 | 0.2 |
| $NH_3/O_2$ | 20.3 | 2.0 | 51.6 | 2.7 | 1.9 | 1.0 | 0.2 | 10.0 | 8.9 | 1.2 | 0.3 |
| $N_2O/O_2$ | 17.0 | 1.3 | 57.9 | 0.4 | 3.5 | 0.1 | 0.0 | 7.2 | 10.4 | 1.9 | 0.3 |

TABLE 2 presents data on the nitrogen contained on stainless steel either without plasma treatment (control) or with plasma treatment and assayed to a depth of 50 Å by x-ray photoelectron spectroscopy. The plasma treatment consisted of either a 45 second exposure to a mixed gas composed of 20 sccm $NH_3$ and 30 sccm $O_2$ or 25 sccm $N_2O$ and 25 sccm $O_2$. The data indicates that the form of the nitrogen changed during the plasma process. The nitrogen changed from a nitride-enriched form in the control specimen, to a form enriched in organic nitrogen ($NH_3/O_2$) or to a form enriched in nitrates ($N_2O/O_2$).

TABLE 2

| | % TOTAL NITROGEN | | |
| --- | --- | --- | --- |
| FORM | No treatment | $NH_3/O_2$ Plasma Treatment | $N_2O/O_2$ Plasma Treatment |
| Nitride | 42.5 | 35.1 | 0 |
| Organic | 41.2 | 49.8 | 56.2 |
| Nitrate | 16.3 | 15.1 | 43.8 |

TABLE 3 presents data on the carbon contained on stainless steel either without plasma treatment (control) or with plasma treatment and assayed to a depth of 50 Å by x-ray photoelectron spectroscopy. The amount of carbon in the form of O—C=O was reduced by either plasma treatment, and in the $N_2O/O_2$ treated specimen the amount of CH was increased.

TABLE 3

| | % TOTAL CARBON | | |
| --- | --- | --- | --- |
| FORM | No Treatment | $NH_3/O_2$ Plasma Treatment | $N_2O/O_2$ Plasma Treatment |
| CH | 58.2 | 59.1 | 73.8 |
| CO | 14.7 | 14.8 | 12.4 |
| O—C=O | 26.5 | 21.9 | 13.8 |

TABLE 4 presents data on the oxygen contained on stainless steel either without plasma treatment (control) or with plasma treatment and assayed to a depth of 50 Å by x-ray photoelectron spectroscopy. The plasma treatment consisted of a 45 second exposure to a mixed gas composed of either 20 sccm $NH_3$ and 30 sccm $O_2$ or 25 sccm $N_2O$ and 25 sccm $O_2$. For the species of oxygen examined, little change was observed between no plasma treatment and treatment with a $NH_3/O_2$ plasma, while treatment with a $N_2O/O_2$ plasma resulted in a decreased amount of C=O and an increased amount of metal oxides.

TABLE 4

| | % TOTAL OXYGEN | | |
|---|---|---|---|
| FORM | No treatment | NH$_3$/O$_2$ Plasma Treatment | N$_2$O/O$_2$ Plasma Treatment |
| Metal Oxide | 43.7 | 46.4 | 55.9 |
| CO | 5.6 | 5.2 | 6.2 |
| C=O | 50.7 | 48.5 | 38.0 |

As plasmas contain very high concentrations of electrons and ions, electrochemical methods may be used to modify surfaces in accord with this invention. Thus, similar results may be obtained using low-energy ion implantation, jet vapor deposition, or atomic layer deposition. Also, plasmas contain high concentrations of free radicals, and therefore chemistries involving free radical alteration of surfaces may be used in accord with this invention.

Subsequent Coatings

Once the plasma has modified the device surface, the device may be used as is or may have additional coatings applied thereto. Suitable materials for additional coatings of the modified surface include plasma-deposited polymers of siloxane, plasma-deposited carbon-based polymers including poly hydroxyethyl methacrylate, polymers coated by dipping or spraying including polymers or derivatives of polyvinyl chloride, polyethylene, polylactide, poly glycolide, poly caprolactone, methyl methacrylate, polyurethane, copolymers of the formentioned, and copolymers of the formentioned containing polyethylene glycol. The polymeric material may also contain a drug introduced by dissolution or dispersion that can be used to augment the effect of the nitrogen-containing and oxygen-containing plasma deposited coating.

Once the surface has been modified by the plasma, such as an N$_3$O/O$_2$ plasma, one or more subsequent coatings or layers, including polymeric coatings, may be applied. In one embodiment, the siloxane surface material described in U.S. Pat. Nos. 5,338,770 and 5,463,010 is used. The siloxane material forms a smooth, continuous thin coating or membrane, and is produced as described in U.S. Pat. Nos. 5,338,770 and 5,463,010. If the siloxane material is used, a plurality of amine functional groups may be bonded to the siloxane surface. The amine groups may then be directly used for further conjugation or further modified to introduce a spacer group. The spacer may be a homo-bifunctional crosslinking agent, a hetero-bifunctional crosslinking agent, or an agent that upon attachment can be modified to produce a reactive site. The spacer may be a linear, branched, or dentimeric material. A similar approach can be used with the other substrate materials using chemistries known to those skilled in the art. A polymeric substance, typically composed of polyethylene glycol, sugars, amino sugars, amino acids, or combinations thereof, may be attached to the spacer to form a microfilm.

Hydrocyclosiloxane Plasma Coating. The membrane is formed through plasma polymerization of suitable aliphatic hydrocyclosiloxane monomers or plasma copolymerization of aliphatic hydrocyclosiloxane monomers and co-monomers. Aliphatic hydrocyclosiloxane monomers have the general formula:

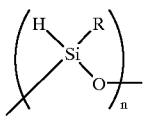

wherein R is alkyl group of 1 to about 5 carbon atoms and n is an integer from 2 to about 10. Monomers include those where n is 7 to 10, where n is 4 to 6 and where n is 2 to 3. Co-monomers such as fluorocarbons, organo-based monomers, or functional group terminated monomers can be utilized to change the properties of the membrane to adjust for varied applications. The monomers are polymerized directly on the substrate surface using plasma-state polymerization techniques. The general process of plasma-state polymerization is known to those in the art. See Yasuda, *Plasma Polymerization,* Academic Press Inc., New York (1985), incorporated herein by reference.

In brief, monomers may be polymerized onto a substrate surface treated with gas plasma composed of molecular species containing oxygen and nitrogen by activating the monomer into a gaseous complex, composed of electrons, ions, gas atoms, free radicals, and molecules in the excited states, known as the plasma state. The plasma state generates highly reactive species, which forms the characteristically highly cross-linked and highly-branched, ultra-thin polymer membrane, which is deposited on the substrate surface as it moves through the area of most intense energy density, known as the plasma glow zone.

In practice, an electric discharge from a radio frequency (R.F.) generator is applied to the "hot" electrodes of plasma reactor. The selected monomers are introduced into the reactor and energized into a plasma, saturating the plasma glow zone with an abundance of energetic free radicals and lesser amounts of ions and free electrons produced by the monomers. As substrate material passes through or remains in the plasma glow zone, the surface of the substrate is continually bombarded with free radicals, resulting in the polymerized membrane coating. The plasma-state polymerized hydrocyclosiloxane membrane is highly adhesive to most organic and inorganic substrates. In one embodiment, plasma polymerization is employed to plasma deposit 1,3,5,7-tetramethylhydrocyclo-tetrasiloxane on the treated surface of the stent or other medical device, utilizing a very short period of plasma deposition, approximately four (4) seconds.

N-protected amines may be plasma grafted to the hydrocyclosiloxane membrane, yielding amine grafted membranes. Suitable N-protected amines include N-trimethylsilyl-allylamine, which may be applied by plasma deposition as described for hydrocyclosiloxane. The period of N-trimethylsilyl-allylamine deposition is again very short, on the order of less than thirty (30) seconds.

Other Polymeric Coatings. In some applications a polymeric substance may be employed to encase the device treated with gas plasma composed of molecular species containing oxygen and nitrogen. A number of polymeric substances can be used, and are known to those skilled in the art. Additional polymeric substances include poly caprolactone, poly lactide, poly glycolide, poly hydroxyethyl methacrylate and co-polymers or derivatives thereof. Other polymeric materials that can be used include posy acrylate, poly bisphenol A carbonate, polybutadiene, polycarbonate, poly butylene terephthalate, posy butryl methacrylate, polydimethyl siloxane, polyester, polyethyleneimine, poly methyl methacrylate, polypropylene, polystyrene, polysulfone, polyurethane, poly vinyl, poly vinyl acetate, polyvinyledine fluoride, and copolymers and variants thereof. The polymeric material may be applied by dipping, immersion, spraying, solvent extraction or other means known in the art. The polymeric substance may be formulated to contain a biological modifier that is anti-inflammatory, non-thrombogenic, anti-angiogenic, or anti-proliferative.

Polyoxyalkylene Coatings. Polyoxyalkylene modified polymeric membranes or coatings are provided that comprise a membrane or coating on a substrate formed from the plasma polymeration of a hydrocyclosiloxane monomer or co-monomer which in turn is on a substrate formed from gas plasma composed of molecular species containing oxygen and nitrogen. These include polyoxyethylene bis-(2-hydroxypyrimidyl) carbonate 1, polyoxyethylene bis-(N-hydroxybenzotriazoyl) carbonate 1, and polyoxyethylene bis-(N-hydroxy-2-pyrrolidinonyl) carbonate 2. The amine grafted hydrocyclosiloxane membranes may be conveniently reacted with the carbonate polyoxyalkylenes to give polyoxyalkylene modified membranes or coatings. In turn, these may be reacted with appropriate bioactive compounds to give the polyoxyalkylene modified membranes or coatings having a polyoxyalkylene tether linking the bioactive compound to the membrane or coating. Bioactive coatings can include aminoglycan polysaccharides, amino polysaccharides, peptides, polypeptides, proteins, compounds having antithrombotic or thrombolytic properties or metal chelators, covalently bonded to the activated polyoxyalkylene groups of the polyoxyalkylene tether.

Medical Devices

The structural component as used herein refers to virtually any device that can be temporarily or permanently implanted into or on a human or animal host. Suitable structural components with a surface include those that are intended to contact blood including stents, catheters, shunts, grafts, and the like. Suitable devices that are intended as tissue implanted include brachytherapy sources, embolization materials, tumor-bed implants, intra-joint implants, materials to minimize adhesions, and the like. The device may include a mesh, coil, wire, inflatable balloon, bead, sheet, or any other structure which is capable of being implanted at a target location, including intravascular target locations, intraluminal target locations, target locations within solid tissue, typically for the treatment of tumors, and the like. The implantable device can be intended for permanent or temporary implantation. Such devices may be delivered by or incorporated into intravascular and other medical catheters. The device can be implanted for a variety of purposes, including tumor treatment, treatment or prophylaxis of cardiovascular disease, the treatment of inflammation, reduction of adhesions, and the like. In one application, the device is used for treatment of hyperplasia in blood vessels which have been treated by conventional recanalization techniques, particularly intravascular recanalization techniques, such as angioplasty, atherectomy, and the like.

Exemplary structural components and devices include intravascular stents. Intravascular stents include including both balloon-expandable stents and self-expanding stents. Balloon-expandable stents are available from a number of commercial suppliers, including from Cordis under the Palmaz-Schatz tradename. Self-expanding stents are typically composed from a shape memory alloy and are available from suppliers, such as Instent. In the case of stents, a balloon-expandable stent is typically composed of a stainless steel framework or, in the case of self-expanding stents, from nickel/titanium alloy. Both such structural frameworks are suitable for use in this invention.

Exemplary devices also include balloons, such as the balloon on balloon catheters. The construction of intravascular balloon catheters is well known and amply described in the patent and medical literature. The inflatable balloon may be a non-dispensable balloon, typically being composed of polyethyleneterephthalate, or may be an elastic balloon, typically being composed of latex or silicone rubber. Both these structural materials are suitable for coating according to the methods of this invention.

The implantable devices will have one or more surfaces or a portion of a surface that is treated with gas plasma composed of molecular species containing oxygen and nitrogen. In the case of stents it is particularly desirable to treat the entire surface. In the case of balloons mounted on catheters it is desirable to coat at least the outer cylindrical surface of the balloon that will be in contact with the blood vessel when the balloon is inflated therein.

In addition to the described devices, a variety of other implantable structures, such as wires, coils, sheets, pellets, particles, and nanoparticles, and the like, may be treated with the gas plasma containing molecular species composed of oxygen and nitrogen according to the methods of the present invention. This includes tissue-implanted brachytherapy sources, embolization materials, tumor-bed implants and the like.

The devices may be introduced to the patient in a conventional manner, depending on the device. In the case of stents, a stent delivery catheter, typically an intravascular balloon catheter in the case of balloon-expanded stents or a containment catheter in the case of self-expanding stents will deliver the stent.

The invention is thought to be particularly useful as applied to cardiovascular stents and for the prevention of restenosis following stent placement, and other interventional treatments, but may also be used in other therapies, such as tumor treatment or in controlling inflammation or thrombosis. Any device in accord with the invention would typically be packaged in a conventional medical device package, such as a box, pouch, tray, tube, or the like. The instructions for use may be printed on a separate sheet of paper, or may be partly or entirely printed on the device package. The implantable device within the package may optionally be sterilized.

The invention is further illustrated by the following non-limiting examples.

EXAMPLE 1

Upon receiving stainless steel stents from the manufacturer, the stents were cleaned by ultrasonication for 60 minutes at 50° C. in a detergent solution (2% Acationox Detergent, Baxter Healthcare Corp.), rinsed with running deionized, charcoal-filtered water for 30 minutes, and then dried at 50° C. in a forced air oven.

Stents were treated in the plasma glow zone of a glow discharge plasma with a mixture of $NH_3/O_2$ for 45 seconds. The plasma was generated at 110 W under a vacuum of 50 mTorr and using a total mass flow rate of 50 standard cubic centimeters per minute (sccm), with a mass flow rate of 25 sccm of $NH_3$ and 25 sccm of $O_2$.

EXAMPLE 2

Stents were treated in the plasma glow zone of a glow-discharge plasma as in Example 1, and thereafter the siloxane derivative, 1,3,5,7-tetramethylhydrocyclo-tetrasiloxane (TMCTS) was polymerized on the stent surfaces in a plasma deposition lasting 4 seconds, with the TMCTS plasma generated at 83 W, 55 mTorr, and a flow rate of 84 sccm.

EXAMPLE 3

Stents treated with $N_3/O_2$ plasma and TMCTS plasma as in Example 2 were placed in a plasma glow zone with N-trimethylsilyl-allylamine (TMSAA), with a 30 second plasma deposition at 65 mTorr, 35 W, and a flow rate of 42 sccm. This resulted in plasma grafting or conjugation of the TMSAA monomer into the stent-bound siloxane polymer, thereby resulting in the integration of a primary amine ($R-NH_2$) into the siloxane polymer.

EXAMPLE 4

Stents of Example 3 were then processed further in a series of wet chemistry steps. In the first of these steps, polyethylene glycol (PEG=3350 $MW_{av}$) was used to prepare the activated-intermediate and bifunctional-crosslinker poly(oxyethylene)bis-(N-hydroxybenzotriazolyl) carbonate, as generally described in U.S. Pat. No. 5,650,234. One end of the poly(oxyethylene)bis-(N-hydroxybenzotriazolyl) carbonate was conjugated to the stent-bound primary amines. During the conjugation, hydroxybenzotriazolyl carbonate was liberated and poly(oxythylene)-(N-hydroxybenzotriazolyl) attached to the amine via a urethane bond. After the removal of excess carbonate, amino dextran (70,000 MW) was attached at pH 8.5 to the other end of the activated intermediate resulting in the covalent binding of amino dextran to polyethylene glycol (PEG), and ultimately to the stent surface. Thereafter, the stents were rinse extensively to remove unbound materials and heat dried.

EXAMPLE 5

Stainless steel wafers (0.75 cm×0.75 cm) were cleaned by ultrasonication for 60 minutes at 50° C. in a detergent solution (2% Acationox Detergent, Baxter Healthcare Corp.), rinsed with running deionized, charcoal-filtered water for 30 minutes, and then dried at 50° C. in a forced air oven. The wafers were treated in a glow-discharge plasma composed of a mixture of $NH_3/O_2$ for 45 seconds. The plasma was generated at 110 W under a vacuum of 50 mTorr and using a total mass flow rate of 50 sccm. For comparative purposes, wafers with no plasma treatment, plasma treatment with only an ammonia plasma, or plasma treatment with only an oxygen plasma were used.

To assess platelet attachment, human blood was obtained from a normal donor who had not received aspirin or other anti-inflammatory medication within one week and collected into heparinized tubes. Thereafter, all manipulations were performed in plastic ware. Platelets were used as platelet-rich plasma and diluted 1:3 with complete medium before use. The medium containing the platelets was added in 0.5 ml aliquots to wells of low-attachment tissue culture cluster plates containing the metal wafers. After two hours the wafers were gently rinsed in phosphate buffered saline, pH 7.4, and the cells fixed by immersing the specimens in buffered formalin. All specimens stained with eosin Y in 70% ethanol, rinsed, and viewed by epifluorescence microscopy. Platelets were viewed at a magnification of 400× and recorded as digitized computer images. Regions of the images evaluated to determine the number of bound cells.

Wafers treated with $N_3/O_2$ plasma had reduced levels of platelet attachment, as shown in FIG. 1

EXAMPLE 6

Stainless steel wafers were prepared as in Example 5. Human blood was obtained from a normal donor who had not received aspirin or other anti-inflammatory medication within one week and collected into heparinized tubes. Thereafter, all manipulations were performed in plastic ware. Leukocytes were isolated by centrifugation over Ficoll-Hypaque, rinsed once in a completed medium composed of Dulbecco's modified Eagle's medium (DMEM) containing 10% fetal bovine serum (FBS) and penicillin/streptomycin, and resuspended in complete medium to a concentration of $10^6$ cells/ml. The medium containing the cells was added in 0.5 ml aliquots to wells of low-attachment tissue culture cluster plates containing the metal wafers. After two hours the wafers were gently rinsed in phosphate buffered saline, pH 7.4, and the cells fixed by immersing the specimens in buffered formalin.

All specimens stained with eosin Y in 70% ethanol, rinsed, and viewed by epifluorescence microscopy. Leukocytes were viewed at 200× and recorded as digitized images. Regions of the images evaluated to determine the number of bound cells.

Figure 2:
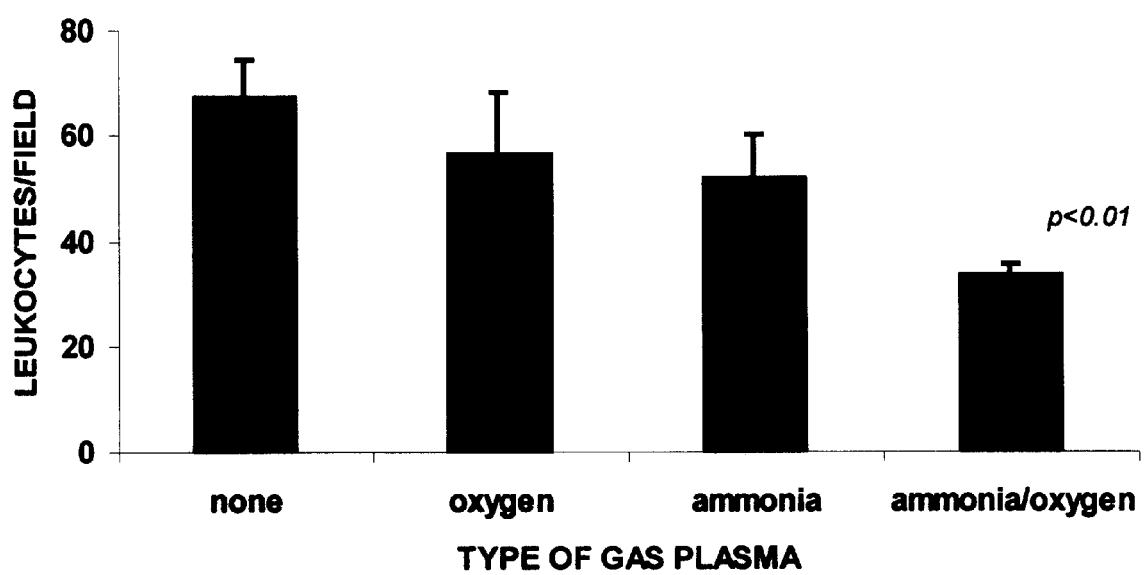
FIG. 2 is a bar graph depicting the attachment of human peripheral leukocytes to stainless steel with and without various gas plasma treatments. Leukocytes were isolated by centrifugation over Ficoll/Hypaque, rinsed, and incubated in tissue culture medium with stainless steel coupons for 1 hour at 37° C. after which the specimens were processed for fluorescence microscopy. Data is presented as the average number of leukocytes/micrograph field ±S.E. Paired t-test was used to assess statistical significance relative to untreated stainless steel.

Wafers treated with $NH_3/O_2$ plasma had reduced levels of leukocyte attachment as shown in FIG. 2

EXAMPLE 7

Stainless steel wafers (0.75 cm×0.75 cm) were treated in a glow-discharge plasma composed of a mixture of $NH_3/O_2$ for 45 seconds as in Example 5. For comparative purposes, stainless steel wafers not subjected to plasma discharge were used.

Wafers were disinfected by UV irradiation or dipping in 70% ethanol and air drying. The wafers were placed in wells of 24 well tissue-culture plates. Aliquots of $10^4$ C3H10 T½ cells were seeded into the wells in Dulbecco's medium containing 10% fetal bovine serum, and antibiotics, and incubated for various periods of time. The medium was gently aspirated, the cultures rinsed once in phosphate buffered saline (PBS), pH 7.4, and the specimens fixed in 10% buffered formalin. After fixation, the cells were permeabilized with 35% ethanol and stained in PBS containing 16 µg/ml of bis-benzimide. In some cases the staining solution also contained 1% bovine serum albumin. After staining, the specimens were rinsed to remove unbound stain, and the specimens examined by epifluorescence microscopy. Cells were scored as apoptotic if the nuclei were blebbed, evidenced condensation of chromatin, evidenced fragmentation of the nucleus.

Figure 3:
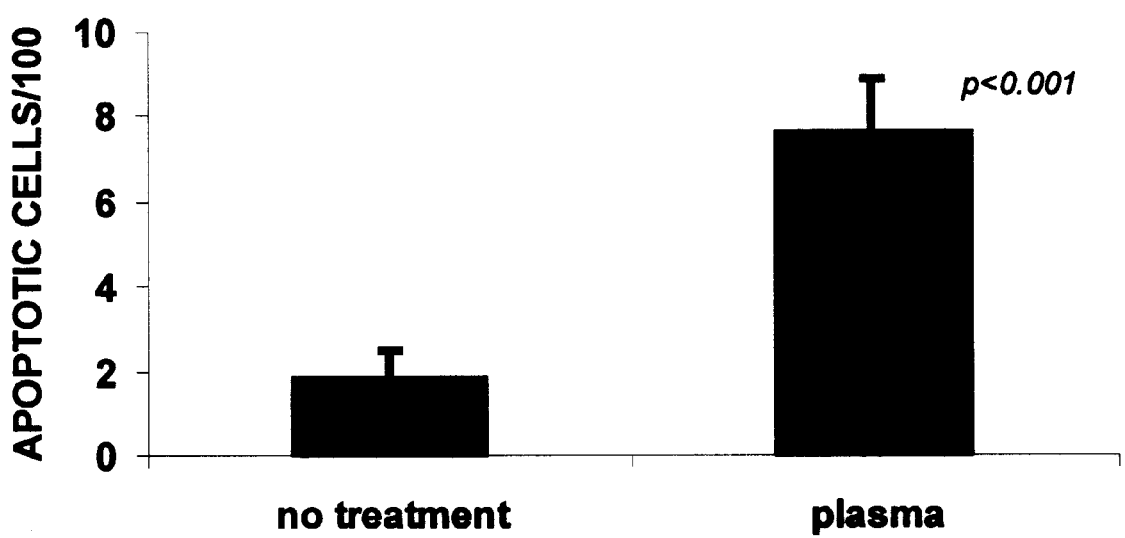
FIG. 3 is a bar graph depicting an increased amount of apopotosis in fibroblasts grown on stainless steel wafers treated with $NH_3/O_2$ plasma. CH310T½ fibroblasts were grown on the wafers for 24 hours, rinsed, fixed in buffered formalin, stained with bis-benzimide, and specimens viewed by fluorescence microscopy. Significance was determined using a paired t-test.

Apoptosis was induced in fibroblasts grown on stainless steel wafers that had been treated with $NH_3/O_2$ plasmas as shown in FIG. 3.

EXAMPLE 8

Polyvinyl chloride and polycarbonate wafers (0.75 cm×0.75 cm) were treated in a glow-discharge plasma composed of a mixture of $NH_3/O_2$ for 45 seconds, with other conditions as in Example 5. For comparative purposes, wafers not subjected to plasma discharge were used.

Wafers were disinfected by UV irradiation and air drying. The wafers were placed in wells of 24 well tissue-culture plates. Aliquots of $10^4$ C3H10T½ cells were seeded into the wells in Dulbecco's medium containing 10% fetal bovine serum, and antibiotics, and incubated for various periods of time. The medium was gently aspirated, the cultures rinsed once in PBS, pH 7.4, and the specimens fixed in 10% buffered formalin. After fixation, the cells were permeabilized with 35% ethanol and stained in PBS containing 16 µg/ml of bis-benzimide. In some cases the staining solution also contained 1% bovine serum albumin. After staining, the specimens were rinsed to remove unbound stain, and the specimens examined by epifluorescence microscopy. Cells were scored as apoptotic if the nuclei were blebbed, evidenced condensation of chromatin, evidenced fragmentation of the nucleus.

Figure 4:
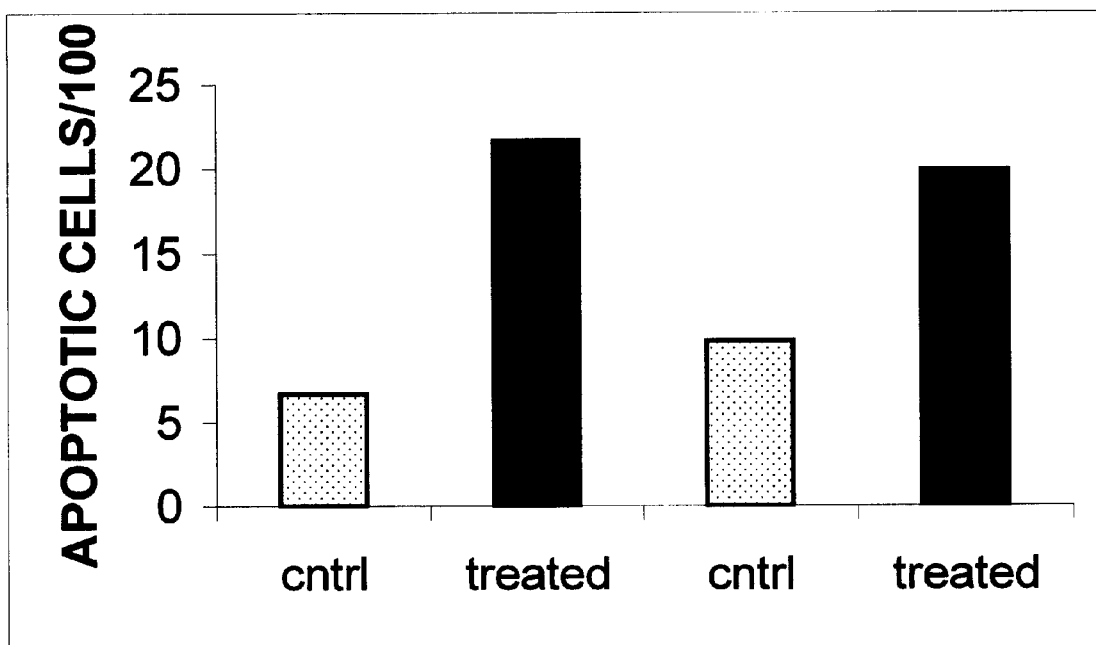
FIG. 4 is a bar graph depicting an increased amount of apopotosis in fibroblasts grown on wafers of either polyvinyl chloride, the two bars on the left, or polycarbonate, the two bars of the right, treated with $NH_3/O_2$ plasma compared to controls which were not plasma treated. CH310T½ fibroblasts were grown on wafers for 24 hours, rinsed, fixed in buffered formalin, stained with bis-benzimide, and specimens viewed by fluorescence microscopy.

Apoptosis was induced in fibroblasts grown on both polyvinyl chloride and polycarbonate wafers that had been treated with $NH_3/O_2$ plasmas as shown in FIG. 4.

EXAMPLE 9

Stainless steel stents, 3×15 mm, were plasma-treated with a mixture of $NH_3/O_2$ for 45 seconds in a glow-discharge plasma as in Example 1, plasma-treated with TMCTS as in Example 2 and TMSAA as in Example 3, and had polyethylene oxide and amino-dextran conjugated as in Example 4.

Stents were then placed in the coronary arteries of swine. The animals were sedated with a combination of ketamine (25 mg/kg), acepromazine (1.1 mg), and atropine (0.6 mg/kg) by intramuscular injection. An intravenous line was established, the animals given methohexital (10 mg/kg), and intubated and ventilated with oxygen (2 L/min), nitrous oxide (2 L/min), and isoflurane 1% (1.5 L/min) using a respirator. All animals were pretreated with aspirin and Ticlopidine 250 mg BID, commencing 24 hours prior to the procedure and for 60 days post-procedure.

After placement of an 8F-introducer sheath in the right carotid artery by surgical cutdown, each animal was given a single dose of heparin (200 units/kg) and bretylium tosylate (2.5 mg/kg). Under fluoroscopic guidance, an 8F hockey stick guiding catheter was positioned in the left coronary ostium.

Stents were implanted in the porcine coronary arteries using a 3.5 mm×17 mm balloon. Following stent implantation, the carotid cut down site was closed and the animals treated with Ticlid and aspirin for a period of 60 days.

Figure 5:
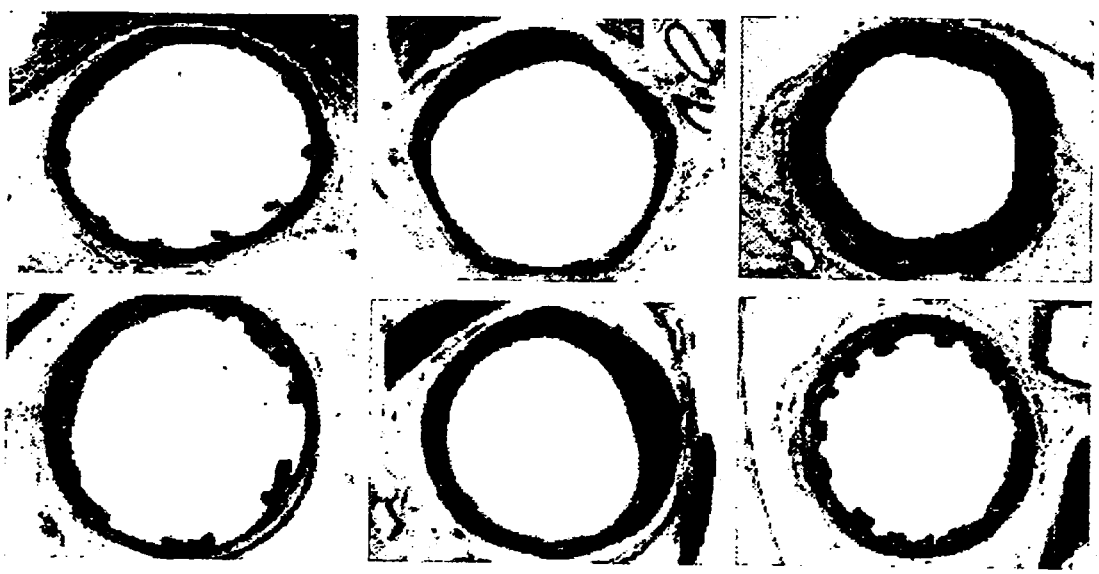
FIG. 5 is a collection of photomicrographs of six different porcine coronary arteries at 2 months after implant of a stent treated with a $NH_3/O_2$ plasma and overcoated with siloxane to which poly(ethylene oxide) and dextran had been conjugated. The arteries are patent, with little or no evidence of smooth muscle infiltration platelet deposition, thrombus formation, or inflammation.

After 60 days, the pigs were returned for a diagnostic angiogram and then euthanized. The stented arteries were studied by histomorphometric techniques. The stented arteries were found to be patent with modest neointima as illustrated for one artery in FIG. 5.

EXAMPLE 10

Stainless steel coupons were evaluated by electron spectroscopy for chemical analysis (ESCA) both without any treatment and following each step in the following manufacturing process:

1) Detergent cleaning;
2) Glow discharge in the presence of ammonia plus oxygen for thirty seconds;
3) Plasma deposition of tetramethyl cyclotetrasiloxane (TMCTS);
4) Plasma deposition of N-trimethylsilyl-allylamine (TMSAA);
5) Conjugation of the bifunctional-crosslinker polyoxyethylene)bis-(1-hydroxybenzotriazolyl) carbonate (HPEO); and,
6) Conjugation of amino dextran (MW 70,000).

ESCA is widely used to investigate the chemical composition of surfaces. The element identification within a given area is obtained by determining the binding energy of back-scattered electrons that are emitted during the exposure to a beam of X-rays. Only electrons released near the surface have enough energy to escape the specimen and be detected, electrons activated below the surface loose their energy in inelastic collisions and are not detected. For a typical ESCA investigation where the surface composition is unknown, a broad survey scan spectrum is obtained first to identify the elements present. Once the elemental composition has been determined, detailed high-resolution scan of selected peaks can be used for the purpose of chemical state identification. As the X-rays have limited penetrating power, ESCA evaluates materials to a thin depth of about 50 Å depending on the initial angle of the X-ray beam.

The steel coupons without any treatment (Steel) had a high percentage of oxygen, carbon, and iron (TABLE 5) when analyzed by ESCA, but no nitrogen. Glow discharge etching with $NH_3/O_2$ resulted in the introduction of nitrogen. Relative to the stainless steel coupon, all subsequent manufacturing steps added material to the surface, therefore resulting in an apparent decrease in the percentage of iron and chromium. The apparent decrease in Fe and Cr is reflective of material being deposited over the coupon.

TABLE 5

| | COMPOSITION IN ATOMIC % | | | | |
|---|---|---|---|---|---|
| | Fe | Cr | O | N | C |
| Steel | 13.7 | 1.3 | 61 | n.d. | 24.5 |
| $NH_3/O_2$ | 1.9 | 0.9 | 58.9 | 7.9 | 20.2 |
| TMCTS | 1.1 | 0.6 | 50.9 | 5.4 | 22.2 |
| TMSAA | 1.6 | 0.1 | 33.5 | 5.7 | 39.7 |
| HPEO | 1.6 | 0.9 | 54.9 | 3.9 | 26.1 |
| Dextran | 1 | 0.6 | 52.9 | 3.5 | 33.6 | n.d. = not detected

In the $NH_3/O_2$ plasma etching step, the relative amount of iron decreased by nearly 12% relative to the untreated steel coupon. Smaller relative decreases were observed in the content of chromium, oxygen, and carbon. The relative amount of nitrogen increased to 7.9% from not being detectable.

EXAMPLE 11

Increasing the plasma treatment time was unexpectedly found to not be proportional to the detected amounts of the relative atomic species, particularly nitrogen. This was found following a 7 minute etching time, as shown in TABLE 6. The most pronounced change was in the nitrogen content, which decreased from 7.9% after 30 seconds to being not detectable after a 7-minute plasma treatment period.

TABLE 6

| | COMPOSITION IN ATOMIC % | | | | |
|---|---|---|---|---|---|
| SECONDS | Fe | Cr | O | N | C |
| 0 | 13.7 | 1.3 | 61 | 0 | 24.5 |
| 30 | 1.9 | 0.9 | 58.9 | 7.9 | 20.2 |
| 420 | 5.3 | 1.2 | 70.2 | 0 | 15.2 |

EXAMPLE 12

High resolution ESCA analysis of stainless steel following glow discharge with $NH_3/O_2$ as a function of the length of the discharge demonstrated that nitrogen species are introduced with discharge times as short as 5 seconds. Two nitrogen peaks were detected, the N1 and N2 peaks. The N1 type is indicative of N—C or N—H bonds, and had the highest deposition around 45 seconds. The N2 type was detectable for discharge times up to 60 seconds, but not thereafter. The N2 type is indicative of N—O bonds and had the highest concentration between 15 and 45 seconds. The results are shown in TABLE 7.

TABLE 7

| Spectral Line | ESCA ATOMIC % FOLLOWING $NH_3/O_2$ PLASMA TREATMENT PLASMA ETCHING TIME IN SECONDS | | | | | | | | |
|---|---|---|---|---|---|---|---|---|---|
| | 5 | 10 | 15 | 30 | 45 | 60 | 120 | 240 | 420 |
| Fe2O3 | 4.4 | 3.9 | 4.2 | 5.1 | 4.3 | 4.5 | 5.6 | 5.5 | 4.1 |
| Fe | 5.5 | 4.8 | 4.9 | 6.3 | 5.6 | 5.5 | 2.7 | 6.4 | 5.4 |
| CrO | 0.8 | 0.9 | 0.8 | 1.0 | 1.0 | 1.0 | 1.0 | 1.4 | 1.0 |
| Cr | 0.2 | n.d. | 0.2 | 0.3 | 0.2 | 0.2 | n.d. | 0.4 | 0.2 |
| O2 | 23.8 | 24.8 | 22.9 | 24.2 | 24.1 | 25.0 | 25.7 | 23.2 | 25.9 |
| O1 | 30.6 | 30.5 | 29.0 | 31.3 | 31.5 | 31.4 | 36.6 | 31.8 | 36.3 |
| N2 | 0.8 | 0.6 | 1.1 | 0.5 | 1.1 | 0.6 | n.d. | n.d. | n.d. |
| N1 | 5.3 | 7.0 | 7.2 | 6.0 | 7.4 | 6.4 | 4.1 | 6.9 | 5.1 |
| C3 | 6.5 | 6.8 | 7.2 | 5.5 | 5.7 | 6.8 | 4.2 | 2.5 | 4.8 |
| C2 | 5.8 | 4.9 | 4.5 | 4.1 | 4.0 | 3.7 | 2.7 | 4.4 | 3.8 |
| C1 | 13.4 | 11.1 | 11.3 | 12.8 | 10.9 | 12.1 | 10.9 | 15.1 | 11.3 |
| Si 2p | 2.9 | 4.8 | 4.2 | 2.9 | 4.2 | 2.8 | 4.6 | 2.5 | 2.2 | n.d. = not detected

Stainless steel surfaces treated in a glow discharge of ammonia alone, that is without oxygen, did not have any detectable N2, although a pronounced N1 peak was found.

Collectively, the data from the ESCA analysis of the surfaces exposed to ammonia/oxygen demonstrate that two types of chemical state of nitrogen are being deposited.

EXAMPLE 13

Stainless steel wafers (0.75 cm ×0.75 cm) were cleaned by ultrasonication for 60 minutes at 50° C. in a detergent solution (2% Acationox Detergent, Baxter Healthcare Corp.), rinsed with running deionized, charcoal-filtered water for 30 minutes, and then dried at 50° C. in a forced air oven. The wafers were treated in a glow discharge plasma composed of a mixture of $N_2O$ and $O_2$ for 45 seconds. The plasma was generated at 110 W under a vacuum of 50 mTorr and using a mass flow rate of 25 sccm of $N_2O$ and 25 sccm of $O_2$. The wafers so treated exhibited a decrease in lymphocyte attachment and platelet attachment relative to untreated stainless steel wafers, and also increased the amount of apoptosis in C3H10T½ cells.

Figure 6:
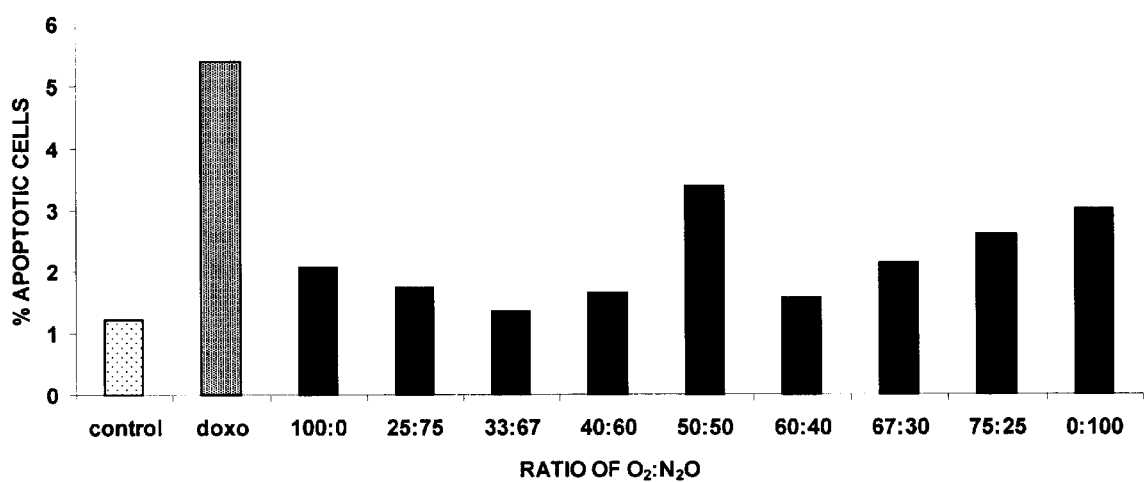
FIG. 6 is a bar graph depicting apoptosis of C3H10T½ cells cultured for 1 day on stainless steel wafers with and without (control) treatment with various combinations of $N_2O$ and $O_2$. The total flow rate for both gases was 25 sscm, and the ratios are the flow rate ratios. Doxorubicin (doxo) was used as a positive control compound to induce apoptosis. Apoptosis was assayed following staining of the specimens with bis-benzimide.

The ratio of $O_2$ to $N_2O$ was then varied, and the percentage of apoptotic cells determined on each, using doxorubicin (doxo) as a positive control compound to induce apoptosis. The results are shown in FIG. 6. Decreased attachment of lymphocytes and platelets was observed at $O_2$ to $N_2O$ ratios of 40:60 to 60:40.

EXAMPLE 14

Stainless steel wafers were coated as in Example 1 with $NH_3/O_2$ was plasma deposited at 20 sccm for $NH_3$ and 30 sccm for $O_2$ for 45 seconds. The contact angle was determined, and compared to the contact angle of the stainless steel wafer not subjected to plasma treatment with NH3/O2, but otherwise similarly processed. The contact angle on the stainless steel without plasma treatment with $NH_3/O_2$ was 39°, while the contact angle after plasma treatment with $NH_3/O_2$ was 15°.

EXAMPLE 15

Two stainless samples were prepared, one using the method of Example 13 in which $N_2/O_2$ was plasma deposited at 25 sccm for each of $N_2O$ and $O_2$ for 45 seconds, and one using the method of Example 1 in which $NH_3/O_2$ was plasma deposited at 20 sccm for each of $NH_3$ and $O_2$ for 45 seconds. X-ray photoelectron spectroscopy (XPS) was conducted in a Physical Electronics Model 5802 Multitechnique system with a monochromatic aluminum anode and an analysis area of approximately 0.8 mm ×2.0 mm. The samples were analyzed in survey mode for overall surface composition, and each element detected on the surface was then analyzed in high energy resolution for binding energy determination.

EXAMPLE 16

Figure 7:
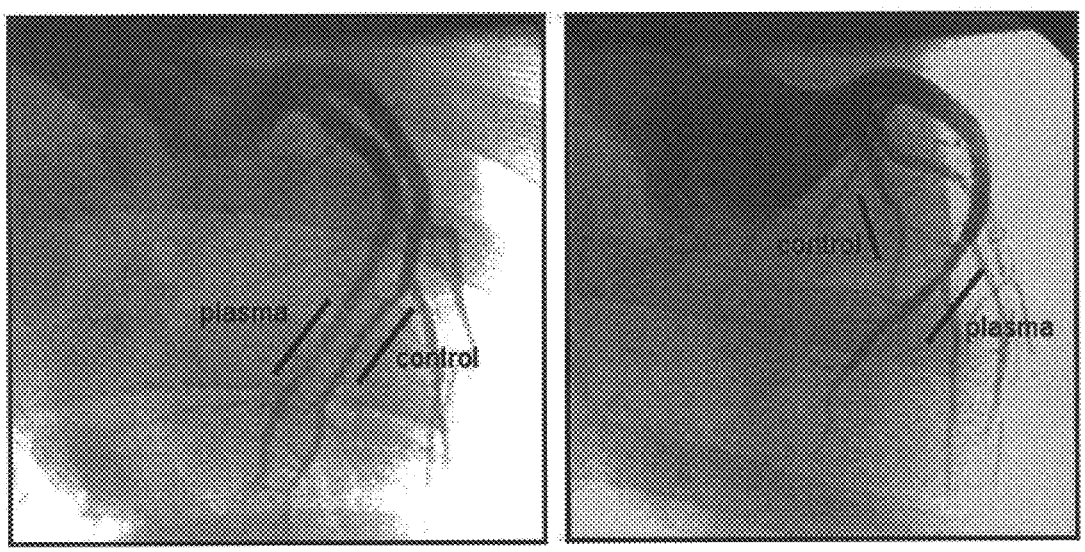
FIG. 7 is a collection of angiogram images of two different porcine hearts at 2 months after implant of stents in an animal model of human restenosis. The stents were either treated with a $NH_3/O_2$ plasma (plasma) or left untreated stents (control). The bars are juxtaposed next to the position of the stents within the arteries. The arteries implanted with plasma treated stents are more patent than the arteries implanted with untreated stents.

Stainless steel stents, 3×15 mm, were plasma-treated with a mixture of $NH_3/O_2$ for 45 seconds in a glow-discharge plasma as in Example 1. Plasma-treated stents and untreated stents were then placed in porcine coronary arteries as in Example 9 and examined by angiography at two months post-implant. The plasma-treated stents were significantly more patent than untreated stents, as shown in FIG. 7.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An implantable medical device with a plasma-modified surface, comprising
   structure adapted for implantation into a patient, the structure comprising at least one metallic contacting surface for contacting a bodily fluid or tissue, wherein the metallic contacting surface is modified by plasma treatment in a plasma comprising nitrogen-containing molecules and oxygen-containing molecules.

2. The device of claim 1, wherein the nitrogen-containing molecules each comprise no more than six atoms.

3. The device of claim 2, wherein the nitrogen-containing molecules each comprise four or fewer atoms.

4. The device of claim 1, wherein the nitrogen-containing molecules are molecules selected from the group consisting of $NH_3$, $(NH_4)^+$, $N_2O$, $NO$, $NO_2$ and $N_2O_4$.

5. The device of claim 1, wherein the oxygen-containing molecules are molecules selected from the group consisting of $O_2$ and $O_3$.

6. The device of claim 1, wherein the plasma treatment with the nitrogen-containing molecules and the oxygen-containing molecules is simultaneous.

7. The device of claim 1, wherein the plasma-modified contacting surface exhibits decreased adhesion of at least some mammalian cells, compared to a similar contacting surface that is not plasma-modified.

8. The device of claim 7, wherein the mammalian cells are cells selected from the group consisting of platelets and leukocytes.

9. The device of claim 1, wherein the medical device is a stent and wherein the at least one contacting surface comprises the lumen of the stent.

10. The device of claim 9, wherein the plasma-modified contacting surface comprising the lumen of the stent exhibits decreased restenosis subsequent to placement in a blood vessel, compared to a similar stent that is not plasma-modified.

11. The device of claim 1, wherein the plasma treatment is for less than about five minutes.

12. The device of claim 11, wherein the plasma treatment is for less than about two minutes.

13. The device of claim 11, wherein the plasma treatment is for less than about one minute.

14. The device of claim 11, wherein the plasma treatment is for between about thirty seconds and about one minute.

15. The device of claim 1, wherein the plasma treatment is of a plasma wherein the nitrogen-containing molecules are $NH_3$ and the oxygen-containing molecules are $O_2$.

16. The device of claim 15, wherein the mass flow rate during plasma treatment of each of $NH_3$ and of $O_2$ is a between a ratio of about 1.5:1 and about 1:1.5.

17. The device of claim 1, wherein the plasma treatment is of a plasma wherein the nitrogen-containing molecules are $N_2O$ and the oxygen containing molecules are $O_2$.

18. The device of claim 17, wherein the mass flow rate during plasma treatment of each or $N_2O$ and of $O_2$ is between a ratio of about 1.5:1 and about 1:1.5.

19. The implantable medical device of claim 1, where the implantable medical device is a member selected from the group comprising stents, catheters, balloons, shunts, grafts, valves, pacemakers, pulse generators, cardiac defibrillators, spinal stimulators, brain stimulators, sacral nerve stimulators, leads, inducers, sensors, seeds, screws, anchors, anti-adhesion sheets, plates and joints.

20. A method of imparting bioactive properties to a contacting surface for contacting a bodily fluid or tissue of an implantable medical device, comprising providing a structure adapted for implantation into a patient, the structure comprising a metallic contacting surface for contacting a bodily fluid or tissue; and modifying the metallic contacting surface by plasma treatment with a plasma comprising nitrogen-containing molecules and oxygen-containing molecules.

21. The method of claim 20, wherein the nitrogen-containing molecules comprise no more than six atoms.

22. The method of claim 21, wherein the nitrogen-containing molecules comprises four or fewer atoms.

23. The method of claim 21, wherein the nitrogen-containing molecules are molecules selected from the group consisting of $NH_3$, $(NH_4)^+$, $N_2O$, $NO$, $NO_2$ and $N_2O_4$.

24. The method of claim 20, wherein the oxygen-containing molecules are selected from the group consisting of $O_2$ and $O_3$.

25. The method of claim 20, wherein the plasma treatment with the nitrogen-containing molecules and the oxygen-containing molecules is simultaneous.

26. The method of claim 20, wherein the plasma treatment is for less than about five minutes.

27. The method of claim 26, wherein the plasma treatment is for less than about two minutes.

28. The method of claim 26, wherein the plasma treatment is for less than about one minute.

29. The method of claim 26, wherein the plasma treatment is for between about thirty seconds and about one minute.

30. The method of claim 20, wherein the plasma treatment is of a plasma wherein the nitrogen-containing molecules are $NH_3$ and the oxygen-containing molecules are $O_2$.

31. The method of claim 30, wherein the mass flow rate during plasma treatment with each of $NH_3$ and of $O_2$ is between a ratio of about 1.5:1 and about 1:1.5.

32. The method of claim 20, wherein the plasma treatment is with a plasma wherein the nitrogen-containing molecules are $N_2O$ and the oxygen-containing molecules are $O_2$.

33. The method of claim 32, wherein the mass flow rate during plasma treatment with each of $N_2O$ and of $O_2$ is between a ratio of about 1.5:1 and about 1:1.6.

34. The method of claim 20, wherein the bioactive properties comprise inhibiting adhesion of mammalian calls.

35. The method of claim 34, wherein the mammalian cells are cells selected from the group consisting of platelets and leukocytes.

36. The method of claim 20, wherein the bioactive properties comprise increased apoptosis of mammalian cells.

37. The method of claim 20, wherein the bioactive properties comprise decreased restenosis.

* * * * *